(12) United States Patent
Xu et al.

(10) Patent No.: US 8,802,057 B2
(45) Date of Patent: Aug. 12, 2014

(54) FORCE-INDUCED MAGNETIZATION CONTRAST FOR DIAGNOSIS AND IMAGING

(75) Inventors: Shoujun Xu, Houston, TX (US); Li Yao, Houston, TX (US)

(73) Assignee: University of Houston System, Houston, TX (US)

( * ) Notice: Subject to any disclaimer, the term of this patent is extended or adjusted under 35 U.S.C. 154(b) by 343 days.

(21) Appl. No.: 13/187,585

(22) Filed: Jul. 21, 2011

(65) Prior Publication Data

US 2012/0020892 A1    Jan. 26, 2012

Related U.S. Application Data

(60) Provisional application No. 61/366,675, filed on Jul. 22, 2010.

(51) Int. Cl.
| | | |
|---|---|---|
| *A61K 49/06* | (2006.01) | |
| *G01N 33/50* | (2006.01) | |
| *A61K 49/18* | (2006.01) | |
| *G01N 33/543* | (2006.01) | |
| *G01N 33/532* | (2006.01) | |

(52) U.S. Cl.
CPC ........ *A61K 49/1872* (2013.01); *G01N 33/5014* (2013.01); *G01N 33/54326* (2013.01); *G01N 33/532* (2013.01)
USPC ....................................... 424/9.34

(58) Field of Classification Search
CPC ................................. A61K 49/1872
USPC ....................................... 424/9.34
See application file for complete search history.

(56) References Cited

U.S. PATENT DOCUMENTS

| 5,238,811 A | 8/1993 | Fujiwara et al. |
| 5,252,493 A | 10/1993 | Fujiwara et al. |
| 2005/0100930 A1 | 5/2005 | Wang et al. |
| 2007/0254375 A1 | 11/2007 | Tsukamoto et al. |

FOREIGN PATENT DOCUMENTS

WO    2007107858 A1    9/2007

OTHER PUBLICATIONS

Yao, L et al., "Forced-Induced Remnant Magnetization Spectroscopy for Specific Magnetic Imaging of Molecules," Angewandte Chemie International Ed., vol. 50, No. 19, pp. 4407-4409 (Apr. 2011).
International Application No. PCT/US2011/044780 Search Report and Written Opinion dated Mar. 16, 2012, 7 pages.

*Primary Examiner* — Jake Vu
(74) *Attorney, Agent, or Firm* — Conley Rose, P.C.

(57) ABSTRACT

A method of detecting target molecules comprising; conjugating a first magnetic particle to a first ligand to form a first magnetic particle ligand conjugate; adding the conjugate to a sample containing target molecules to form a mixture comprising, the free conjugate and conjugate-target molecule binding pairs; measuring a first magnetization of the mixture; subjecting the mixture to a first force; measuring a second magnetization value of the mixture; subtracting the second magnetization value from the first magnetization value to calculate a first force-induced magnetization contrast; subjecting the mixture to a second force; measuring a third magnetization of the mixture; and subtracting the third magnetization value from the second magnetization value to calculate a second force-induced magnetization contrast.

16 Claims, 13 Drawing Sheets

FORCE-INDUCED MAGNETIZATION CONTRAST FOR DIAGNOSIS AND IMAGING

CROSS-REFERENCE TO RELATED APPLICATIONS

This application claims the benefit under 35 U.S.C. §119(e) of U.S. Provisional Application No. 61/366,675 filed on Jul. 22, 2010, the disclosure of which is hereby incorporated herein by reference.

STATEMENT REGARDING FEDERALLY SPONSORED RESEARCH OR DEVELOPMENT

Non applicable.

BACKGROUND

1. Field of the Invention

The present invention relates to a method for the diagnosis of diseases using magnetic entities to target one or more specific molecules that are indicators of a specific disease. The resulting diagnosis may be carried out in vitro, using for example microchip analysis, or in vivo where for example, magnetic entities are injected into a subject. This invention also relates to security check and toxicity analysis. Some embodiments of this method may be used for identifying and quantifying the presence of a target molecule or target molecules in a single sample and elucidating conformational information about such target molecules.

2. Background of the Invention

Magnetic entities, most often as particles and in other forms such as rods and shells, are widely used in medical diagnosis and imaging. Usually they are conjugated with ligands that specifically target one or more molecules (receptors) which serve as indicators for certain diseases or are representative of biological hazards. One major challenge is to distinguish the signal that is specific to magnetic entities that are bound to the target molecules from the background signal of free, unbound magnetic entities. When such a distinction cannot be efficiently achieved, the alternative is to use physical separation to isolate the bound magnetic entities from the free magnetic entities. However, such a procedure is highly undesirable for most applications, due in part to excessive toxicity and increased cost.

Existing methods used to measure specific binding, without the use of separation techniques include: nuclear relaxation contrast, magnetic particle relaxation contrast, nonlinear response of susceptibility, and remanence detection. However, all of these methods have limitations which prevent their broad use in clinical settings. For example, nuclear relaxation contrast has poor sensitivity because of the intrinsically weak signal of nuclear spins. Magnetic particle relaxation contrast is based on the difference in relaxation times between the bound magnetic particles and the free magnetic particles. Associated shortcomings include a small difference in relaxation time and a narrow time window during which the measurement can be performed. Also, it is known that susceptibility response is severely affected by the size distribution of the particles. Remnant field measurement offers high sensitivity, but a strong background signal from the free particles results in a lower sensitivity and selectivity.

The production of a method capable of revealing multiple types of target molecules based on their different binding properties would be particularly well received, and embodiments of the herein presented method are believed to overcome certain above mentioned limitations by the utilization of force-induced contrast in magnetization measurements.

BRIEF SUMMARY OF THE DISCLOSED EMBODIMENTS

These and other needs in the art are addressed in one embodiment by a method of detecting target molecules comprising; conjugating a first magnetic particle to a first ligand to form a first magnetic particle ligand conjugate; adding said conjugate to a sample containing target molecules to form a mixture comprising, free conjugate and conjugate-target molecule binding pairs; measuring a first magnetization of said mixture; subjecting said mixture to a first force; measuring a second magnetization value of said mixture; subtracting said second magnetization value from said first magnetization value to calculate a first force-induced magnetization contrast; subjecting said mixture to a second force; measuring a third magnetization of said mixture; and subtracting said third magnetization value from said second magnetization value to calculate a second force-induced magnetization contrast. In some embodiments the measuring comprises atomic magnetometers, superconducting quantum interference devices, giant magnetoresistive sensors, nuclear magnetic resonance, or combinations thereof.

In other embodiments the force is selected from the group consisting of mechanical shaking force, fluid dragging force, magnetic force, ultrasonic force, centrifugal force, electrical force and combinations thereof. Some embodiments of the method further comprise performing a force scan, whereby the force is scanned over a range of 5 pN to 2000 pN while measuring magnetization decrease as a function of the force. In other embodiments of the method the force scan is produced by varying flow rate, shaking speed, sound wave amplitude, magnetic field gradients, or electrical field amplitude.

In some other embodiments the sample is in a sample holder, in other embodiments the mixture is in a liquid environment. In further embodiments of the method, the force is adjusted by changing the shape of the sample holder, the level of liquid in the sample holder or combinations thereof.

Other embodiments of the method further comprising a second conjugate; wherein said second conjugate is different from said first conjugate, and said second conjugate forms a target molecule second conjugate binding pair, wherein said second conjugate binding pair produces a different FIRM peak than the first conjugate binding pair, thereby allowing the identification of different target molecules with similar binding force constants. In some embodiments, the second conjugate differs from the first conjugate by chemical composition, shape, size, magnetic properties, ligand, magnetic coating properties or combinations thereof.

In other embodiments the method further comprises; plotting magnetization by force and calculating a derivative; and plotting the derivative by force to produce a force-induced remnant magnetization spectrum. In some of the embodiments described herein, the method further comprises quantifying the number of peaks present in the spectrum and identifying the number of different target molecule species in the sample, based on said quantifying. In other embodiments the method further comprises analyzing the shape of the peaks in the spectrum to obtain conformational information about the target molecules, based on said analyzing.

Other embodiments of the method further comprises; after measuring a third magnetization, adding conjugate and rebinding said conjugate to said target molecules; and measuring a fourth magnetization value, wherein said fourth magnetization value is about 75% to about 100% of the second magnetization value and confirming specific molecular binding.

In some embodiment of the method the sample is selected from the group comprising natural molecules, synthetic molecules, biological tissue, biological cells or combinations thereof, in other embodiments the sample is immobilized on a surface, wherein said surface is derivatized or non-derivatized. In further embodiments the sample is an animal or human body and said adding is by injection or by ingestion. In other embodiments the sample is a chemical sample or biochemical sample for security checking, and in further embodiments the sample is a chemical sample or biochemical sample in a toxicity screen.

Thus, embodiments described herein comprise a combination of features and advantages intended to address various shortcomings associated with certain medical diagnostic and magnetic imaging methods. The various features and characteristics described above, as well as others, will be readily apparent to those skilled in the art upon reading the following detailed description, and by referring to the accompanying drawings.

BRIEF DESCRIPTION OF THE DRAWINGS

For a detailed description of the disclosed embodiments of the invention, reference will now be made to the accompanying drawings, wherein:

FIG. 10B shows a plot illustrating relative magnetizations of two rebinding tests compared to the first binding experiment to confirm that the dissociation is of specific molecular bonds within the target-molecule-magnetic particle-conjugate.

DETAILED DESCRIPTION OF DISCLOSED EMBODIMENTS

Figure 1:
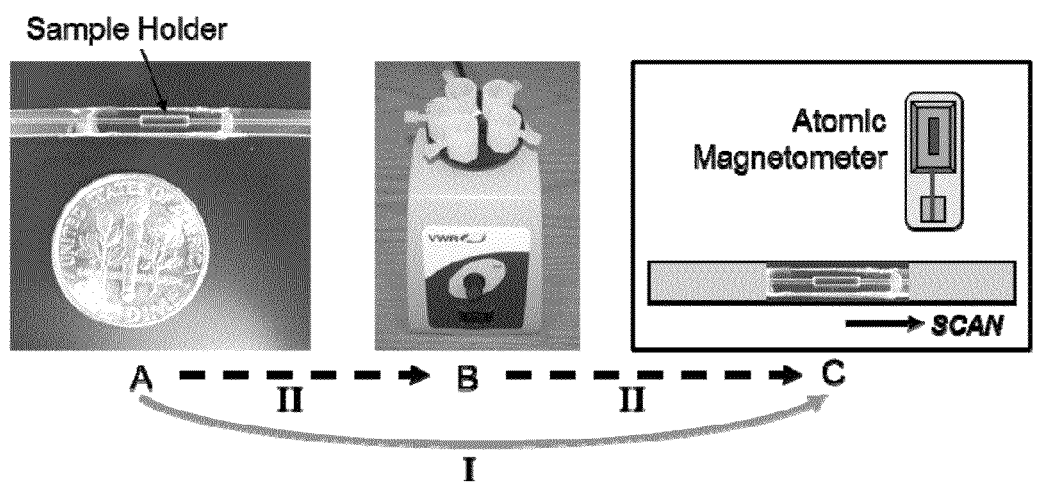
FIG. 1 depicts an example of an apparatus used in an embodiment of the method described herein to measure the force-induced magnetization contrast of a sample.

Embodiments herein addressed are intended to overcome certain above mentioned limitations by using a force-induced contrast in magnetization. In embodiments of the method, the magnetic signal of the sample containing magnetic particles and target molecules is a function of an externally applied force. When the force equals zero, all the magnetic particles contribute to the recorded signal, whereby the measured magnetization will be at a maximum. A gradually increasing force is then exerted on the sample and magnetization is measured at each force. The physisorbed magnetic particles, which have the weakest binding strength dissociate from the sample or sample holder surface first. The dissociated particles undergo Brownian relaxation, resulting in the dissociated magnetic particles no longer contributing to the magnetic signal and a decrease in the measured magnetization value compared to the original value obtained from the measurement without an external force.

In some embodiments the magnetic particles are conjugated to ligands which comprise atoms or molecules that are selective for target molecules, thereby forming magnetic particle ligand conjugates that bind only specific target molecules to form binding pairs As the applied force increases, magnetic particle ligand conjugates with a weak bonding force to their corresponding target molecules start to dissociate and undergo Brownian relaxation, resulting in another decrease in the measured magnetization. Such a change in the measured magnetizations, herein termed as "magnetization contrast", is a quantitative measurement of each of the binding pairs (magnetic particle ligand conjugate and target molecule) present in the sample. The selectivity among the different binding pairs that are present in the sample is based on the binding force between a given type of magnetic particle ligand conjugate and its corresponding target; each pair having its own discrete interaction force. In the simplest case where there is only one type of target molecule, the reduction in magnetization is due to the dissociation of nonspecifically bound, or physisorbed, magnetic entities.

By taking the derivative of the magnetization versus the force, a spectrum is obtained, the spectrum herein termed as force-induced remnant magnetization (FIRM) spectrum. A FIRM spectrum contains a series of negative peaks. The position of each peak corresponds to the specific binding force of the magnetically labeled ligand to the target molecule. The absolute amplitude of each peak represents the quantity of the bonds with that specific binding force. Therefore, the binding force is used to quantitatively distinguish molecular bonds and can now be used as spectroscopic character in the field of magnetic imaging.

It is believed that some embodiments of the method described herein provide: (a) selective measurement of target molecules without background interference; and (b) the simultaneous measurement of multiple types of target molecules in a single sample, thereby making such a technique more efficient and cost effective than some conventional methods. From the magnetization contrast and FIRM spectrum, different types of binding pairs can be distinguished based on their respective binding force.

It is further believed that certain embodiments described herein provide; a) a noninvasive method, because detection is based on a magnetic signal and is mechanically and optically decoupled from the molecular system. b) sensitivity, because it detects the magnetic field of the magnetic particles directly. c) a method applicable for opaque conditions and nontransparent samples, unlike optic-based techniques and d) the apparatus associated with this method is portable and inexpensive, allowing for broad applications in remote regions and developing countries.

General components of the FIRMS method described throughout, include: 1) a sample holder which contains a biological sample incubated with magnetic particle ligand conjugate, or a live subject to be diagnosed, injected with such magnetic particle ligand conjugates; 2) a method and device to apply a disturbing force; and 3) a device or apparatus that can measure the magnetization of the magnetic entities.

One embodiment of the present invention includes a representative experimental configuration for performing the method described herein, and is illustrated in FIG. 1. A sample holder (A) is constructed, with dimensions of 4×1×1 mm. For testing purposes, target molecules are coated on the bottom of the sample holder. For diagnostic applications or imaging, the target molecules may be naturally immobilized on their biological host, such as cells. Magnetic particle ligand conjugates are then added to the sample holder.

The magnetization of the total particles, which include the bound particles and unbound (physisorbed) particles, is first measured by scanning magnetic imaging (SMI) using an atomic magnetometer (FIG. 1C, sequence is indicated by solid line), the total magnetization $M_I$ is measured. Then a force with low amplitude is exerted on the molecules in the sample holder, for example, a mechanical force by a mixer (FIG. 1B, step II). After this process, the magnetization of the magnetic particles is measured again by SMI, which we assign as $M_{II}$. The quantity of the bound particles is determined by $M_{II}$. The magnetization difference, $M_I$–$M_{II}$, represents the quantity of physisorbed particles or non-specific binding.

The force is then increased and the magnetization is measured at each increasing step, with the magnetization termed as $M_{III}$, $M_{IV}$ and so on. Each time the force exceeds a specific binding force (bond strength), the corresponding bound magnetic particle ligand conjugate (referred herein as the conjugate or magnetic conjugate) will dissociate, resulting in a decreased magnetization, $M_{III}$. The magnetization contrast, $M_{II}$–$M_{III}$, represents the quantity of the specific target molecules.

Figure 2:
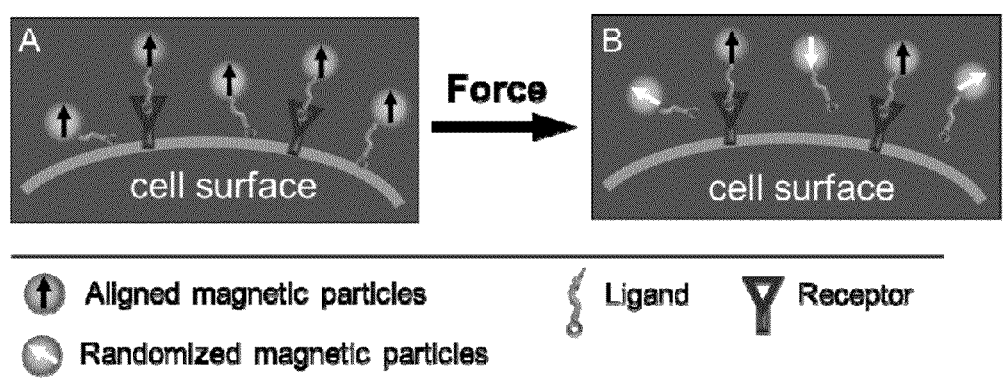
FIG. 2 depicts the randomization of magnetic dipoles by force-induced dissociation after applying a force in accordance with principles described herein.

The principle of force-induced magnetization contrast is further illustrated in FIG. 2. Cells are placed in the sample holder, which contain a specific type of receptor molecule to be targeted by the magnetic conjugate. When the conjugates are incubated with the cells, they can either be physisorbed by the cell surface which is not molecular specific (non-specific binding), or specifically bound to the receptors on cell surface. Before a force is applied (FIG. 2A), all the magnetic conjugates contribute to the measured magnetization $M_I$. After the force is applied, the physisorbed particles will dissociate from the cell surface and undergo Brownian motion, which leads to the randomization of the magnetic dipoles of the dissociated magnetic conjugates. Therefore the only portion of conjugates that produce a measurable magnetization are the ones remaining bound to the cell via the molecular bonds. The measured $M_{II}$ thus represents the quantity of the specific molecular bonds in the system. Increasing the force amplitude will result in selective dissociation of chemical bonds with a different strength ($M_{III}$).

Figure 3:
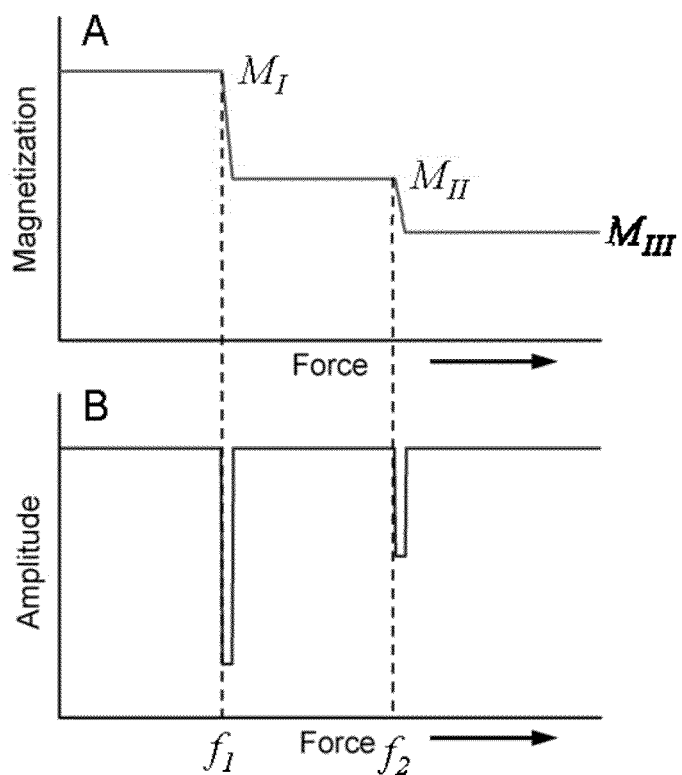
FIG. 3A depicts a simulated magnetization contrast profile and FIG. 3B depicts a FIRM spectrum obtained by taking the derivative of the plot in 3A.

By taking the derivative of the magnetization with regard to the external force a force-induced remnant magnetization (FIRM) spectrum can be produced and as such is illustrated in FIG. 3. As shown, the magnetization contrast (FIG. 3A) and the FIRM spectrum (FIG. 3B) have two binding pairs with different binding forces ($f_1$ and $f_2$ respectively) and in different quantities. For binding with force $f_2$, the quantity of the target molecules is represented by $M_{II}$ minus $M_{III}$; for binding with force $f_1$, the quantity of the target molecules is represented by $M_I$ minus $M_{II}$. $M_{III}$ would be zero if no other binding pair exists in the sample that has a stronger binding constant. From the FIRM spectrum, the widths of the peaks contain information about the force distribution of the binding interaction, due to, for example, the size or the conformational distribution of the target molecules.

Figure 13:
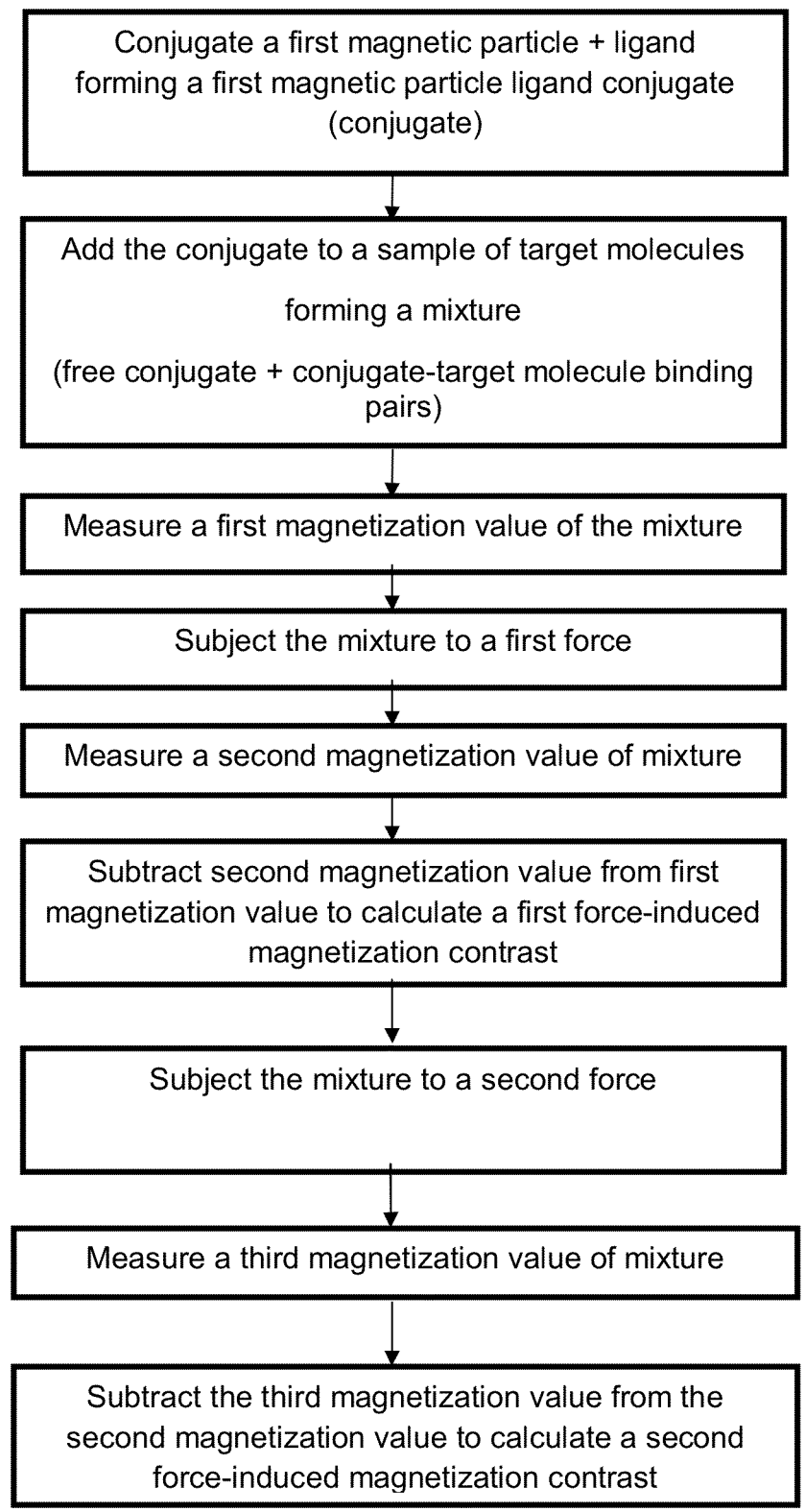
FIG. 13 illustrates a flow chart of a method of detecting target molecules in accordance with principles described herein.

Embodiments are therefore drawn to a method of detecting target molecules comprising; conjugating a first magnetic particle to a first ligand to form a first magnetic particle ligand conjugate; adding said conjugate to a sample containing target molecules to form a mixture comprising, free conjugate and conjugate-target molecule binding pairs; measuring a first magnetization of said mixture; subjecting said mixture to a first force; measuring a second magnetization value of said mixture; subtracting said second magnetization value from said first magnetization value to calculate a first force-induced magnetization contrast; subjecting said mixture to a second force; measuring a third magnetization of said mixture; and subtracting said third magnetization value from said second magnetization value to calculate a second force-induced magnetization contrast. Some embodiments of the method described herein are illustrated in flow diagram of FIG. 13.

In some embodiments, measuring the magnetization is conducted by using scanning magnetic imaging with atomic magnetometers, superconducting quantum interference devices, giant magnetoresistive sensors, nuclear magnetic resonance, or combinations thereof. In certain embodiments, the type of force produced is selected from the group comprising of: mechanical shaking force, dragging fluid force, magnetic force, ultrasonic force, centrifugal force, electrical force or combinations thereof. In further embodiments, a force scan is produced whereby the force is scanned over a range of 5 pN to 2000 pN while measuring the magnetization decrease as a function of the force. Further, in some embodiments, the force is controlled by varying flow rate, shaking speed, sound wave amplitude, magnetic field gradients, or electrical field amplitude.

In some embodiments, the sample is in a sample holder and in other embodiments the mixture is in a liquid environment, wherein the liquid may be selected from distilled water, buffer, saline, blood, and other animal or human fluids. In some embodiments the force is adjusted by changing the shape of the sample holder, the level of liquid in the sample holder or combinations thereof.

In other embodiments, the method herein described, further comprises a second conjugate; wherein the second conjugate is different from the first conjugate, and the second conjugate forms a target molecule second conjugate binding pair, wherein said second conjugate binding pair produces a different FIRM peak than the first conjugate binding pair, thereby allowing the identification of different target molecules with similar binding force constants. In some further embodiments, the second conjugate differs from the first conjugate by chemical composition, shape, size, magnetic properties, ligand, magnetic coating properties or combinations thereof.

Some embodiments of the method described herein comprises plotting the measured magnetization values by force values and calculating a derivative; and further plotting the derivative by force to produce a force-induced remnant magnetization spectrum. In some embodiments of the method described herein, the method comprises quantifying the number of peaks present in the FIRMs spectrum and thereby identifying the number of different target molecule species in the sample. Some embodiments further comprises analyzing the shape of the peaks in the spectrum to obtain conformational information about the target molecules.

Other embodiments of the method further comprise; adding conjugate and rebinding said conjugate to said target molecules; and measuring a fourth magnetization value, wherein said fourth magnetization value is about 75% to about 100% of the second magnetization value, confirming specific molecular binding.

In certain embodiments herein described, the sample is selected from the group comprising natural molecules, synthetic molecules, biological tissue, biological cells or combinations thereof. In further embodiments, the sample is immobilized on a surface, wherein said surface is derivatized or non-derivatized. In other embodiments, the sample is an animal or human body and said adding is by injection or by ingestion. In some embodiments of the method described herein, the sample is a chemical sample or biochemical sample in a toxicity screen. In another embodiment, the sample is a chemical sample or biochemical sample for security checking for example a biohazard, which maybe immobilized onto an appropriate surface, then said conjugates are used to identify and quantify the immobilized biohazard (molecules) on the surface. Similar approaches may be used for screening of illegal substances. As such embodiments Such methods are similarly described in Yao, L. & Xu, S.-J. Force-induced remnant magnetization spectroscopy for specific magnetic imaging of molecules. *Angew. Chem. Int. Ed.* 50, 4407-4409 (2011) which hereby is expressly incorporated herein by reference in its entirety for any purpose. In the event that one or more of the incorporated materials defines a term in a manner that contradicts the definition of that term in this application, this application controls

EXAMPLES

Example 1A

Targeting Biotin Molecules with Streptavidin-Coated Magnetic Particles

A model system using the binding pair of biotin and streptavidin, which is widely used in molecular imaging in biology and medical research, was tested. Biotin molecules were immobilized on the sample holder surface to serve as the target molecules; streptavidin-conjugated magnetic particles served as the probe and are added to the sample holder as previously described.

Figure 4:
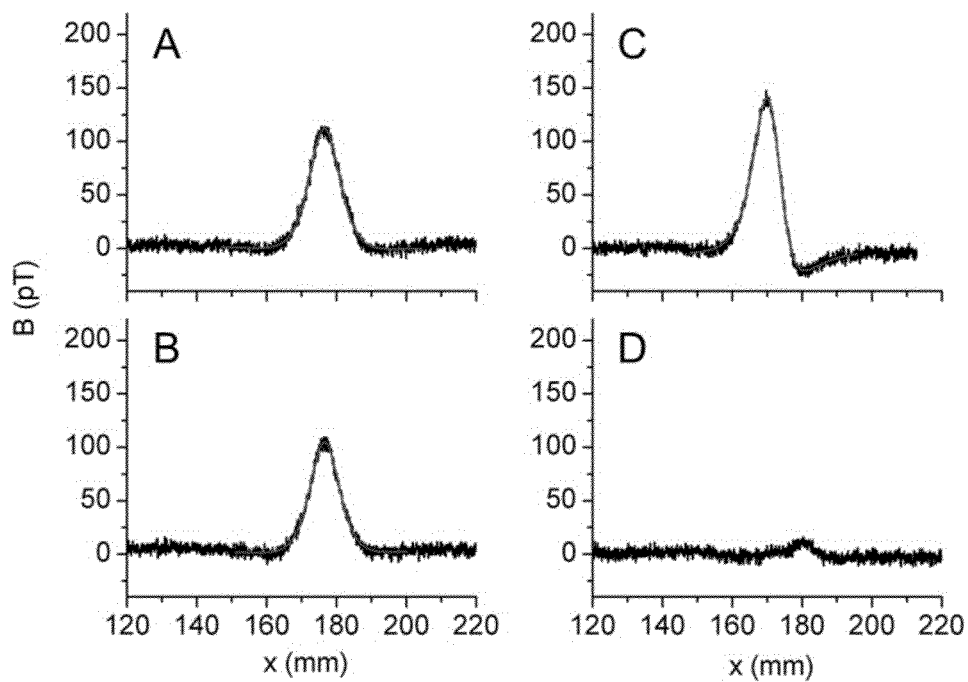
FIG. 4 depicts magnetization measurements for streptavidin-coated magnetic particles and biotin target molecules coated on a glass surface before the application of a force (4A) and after the application of force (4B) and for streptavidin-coated magnetic particles in the absence of biotin before applying a force (4C), and after applying a force (4D)

As a control experiment, another sample holder absent of biotin molecules was also constructed and magnetic particles-streptavidin-conjugates are also added to the control sample holder. The magnetization of each sample holder is measured before and after the application of force and the results presented in FIG. 4. The magnetic signal of the biotin-coated sample holder before applying force with a shaker is displayed in FIG. 4A and after applying force in FIG. 4B. The magnetic signals of the control, before applying force is displayed in FIG. 4C and after, in FIG. 4D. The magnetic field profiles were obtained using scanning magnetic imaging with an atomic magnetometer, from which magnetization and spatial information can be extracted. The results show that the remaining magnetic signal obtained with the biotin-coated cell (FIG. 4B) is significant, due to the specific molecular binding between streptavidin and biotin. In contrast, the magnetic signal of the control is completely removed by force disturbance because of the absence of biotin molecules and therefore the lack of any specific binding (FIG. 4D), the initial signal is from physiosorbance. The magnetizations $M_I$ and $M_{II}$, obtained by fitting the magnetic profiles in FIG. 4A and FIG. 4B respectively, are listed in Table 1 below). From these values it was calculated that 82% of the total magnetic particles were bound, which is obtained from $M_{II}/M_I$, and 18% are free.

TABLE 1

Quantitative analysis of magnetization contrast obtained in FIG. 4A and 4B, where the targeted biotin molecules were present. The magnetization values, in the unit of $A \cdot m^2$, are obtained by fitting the corresponding magnetic field profiles.

|  | Biotin-Streptavidin |
| --- | --- |
| Before ($M_I$) | $5.50 \times 10^{-10}$ |
| After ($M_{II}$) | $4.51 \times 10^{-10}$ |

Example 1B

Figure 5:
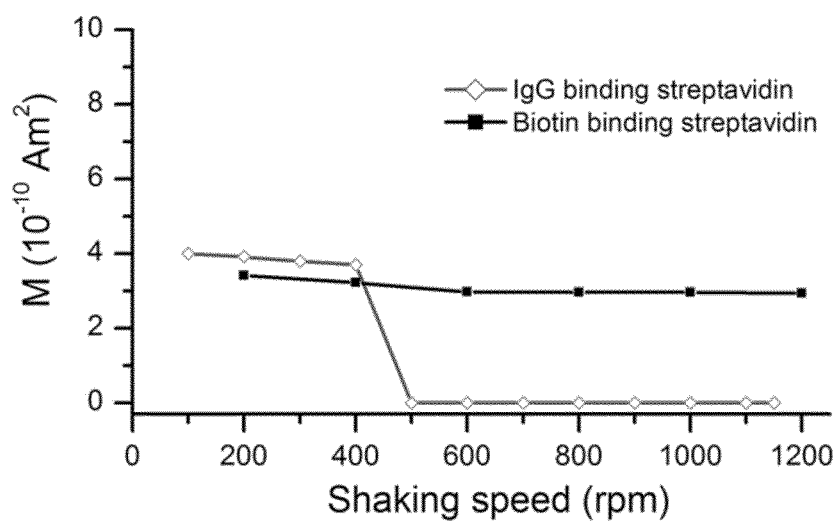
FIG. 5 depicts magnetization contrasts for streptavidin-coated magnetic particles (conjugate) binding to biotin and IgG coated surfaces at increasing forces in accordance with principles described herein.

Targeting Biotin Molecules and IgG with Magnetic Particles-Streptavidin Conjugate A further embodiment is shown in FIG. 5, where more force steps are applied. Again, the molecular binding pair is biotin and streptavidin. The control is a sample holder coated with antibody molecules (mouse IgG), which do not specifically bind to streptavidin. Again magnetization measurements are recorded before and the application of force and after each subsequent application of force for the sample holder containing biotin and streptavidin. This procedure was repeated for the control sample holder. The biotin-streptavidin-magnetic particle complex remains bound after a strong force of 1200 rpm (revolution per minute) from a digital shaker. However the physisorbed particles in the IgG-containing control sample holder underwent complete dissociation at 500 rpm.

Figure 6:
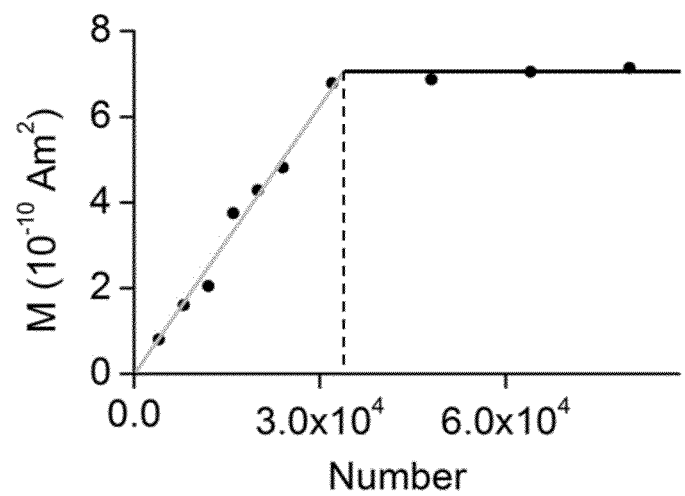
FIG. 6 depicts the saturation of a fixed number of biotin molecules by streptavidin-coated magnetic particles (conjugate) in accordance with principles described herein.

To further confirm that only the bound magnetic particles give measurable signal after exerting a force, various amounts of magnetic particles streptavidin conjugate are loaded onto biotin molecules. For each amount, $M_{II}$ is measured after the cell is subjected to the same force as in FIG. 4. Since the total number of the target biotin molecules on the surface of the sample holder is fixed, it is expected that $M_{II}$ first increases as the amount of the conjugate increases, and then reaches a plateau which represents the total number of biotin molecules available. As shown in FIG. 6, $M_{II}$ first increases linearly then reaches a plateau when no more magnetic particles streptavidin conjugate can bind to the fixed amount of biotin molecules. The current detection limit is a few hundred magnetic particles based on the uncertainty in magnetization values.

Example 2

Targeting Antibody Molecules with Antigen-Coated Magnetic Particles

Figure 7:
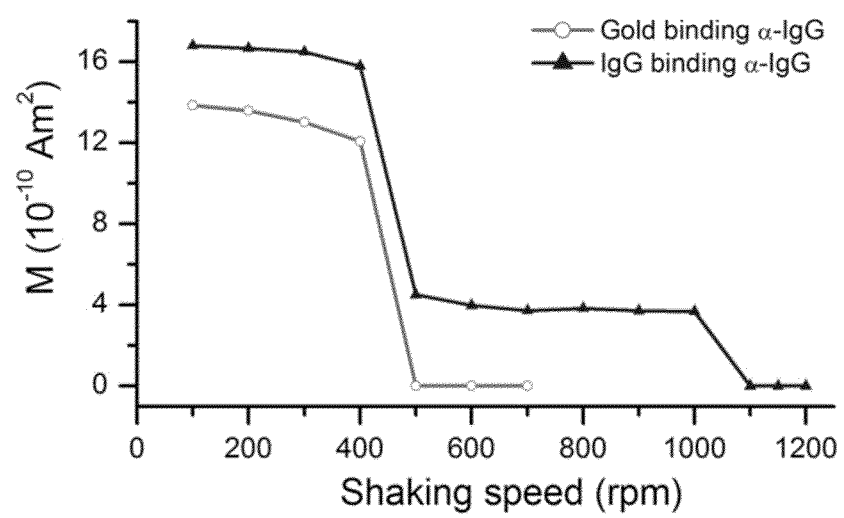
FIG. 7 depicts a force-induced magnetization contrast plot of antibody-antigen binding, where target mouse IgG molecules attached to the bottom surface of a sample holder, are bound by magnetic particle-goat α-mouse IgG (conjugate), and the control plot of bare gold and magnetic particle-goat α-mouse IgG (conjugate), in accordance with principles described herein.

For disease diagnosis, the binding force between target molecules and ligand-conjugated magnetic particles is typically weaker than that of the biotin-streptavidin interaction, as seen for antibody-antigen interactions. In some embodiments, such antibody-antigen interactions have been tested. FIG. 7 illustrates the use of an embodiment of the present invention when the target molecules are mouse IgG immobilized on the surface of the cell and the probe is goat α-mouse IgG-conjugated magnetic particles. The control experiment is a bare gold surface which does not specifically bind with the α-mouse IgG-conjugated magnetic particles. In the sample holder with target IgG, two magnetization contrasts occur, one at 500 rpm and one at 1100 rpm. The former is the dissociation of the physisorbed magnetic particles, and the latter is the dissociation of the bonds between the IgG and the α-IgG-conjugated magnetic particles. The control experiment displayed only physisorption, so the magnetization became zero after applying a force of 500 rpm.

Contrasted to the biotin-streptavidin experiment, one aspect of this antibody-antigen experiment is that at the same force, the magnetization for the latter is zero, while it is not zero for the former. This difference is consistent with the fact that antibody-antigen binding is much weaker than that of biotin-streptavidin interaction, meaning a certain force that is sufficient to break antibody-antigen bond may not be strong enough for breaking the biotin-streptavidin pairs. This indicates that this method can distinguish the presence of different types of ligand-receptor pairs by tuning the applied force.

Figure 8:
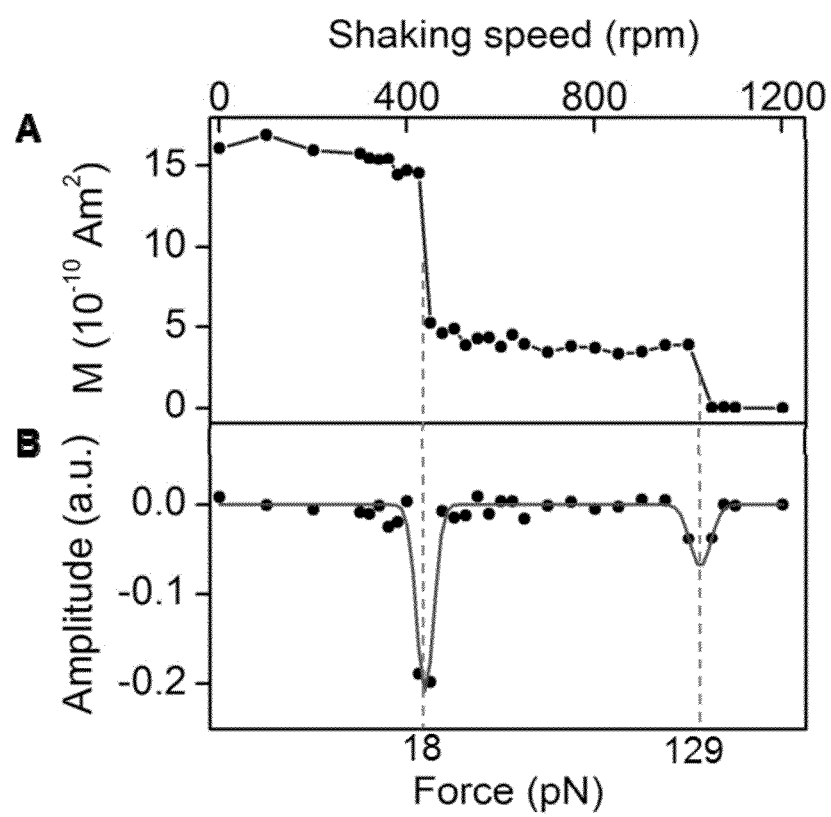
FIG. 8 depicts a high-resolution magnetization contrast vs. force plot with fine force steps (8A) and the corresponding FIRM spectrum (8B)

FIG. 8 shows magnetization contrast with finer force increment (FIG. 8A) and its corresponding FIRM spectrum (FIG. 8B). Fitting with Gaussian functions for the spectrum produces two peaks, one at 437 rpm and another one at 1025 rpm. The calibration of force may be achieved by taking literature values for the corresponding binding pairs of known receptor-ligand/binding pair interactions or applying a force that can be easily calculated.

Figure 9:
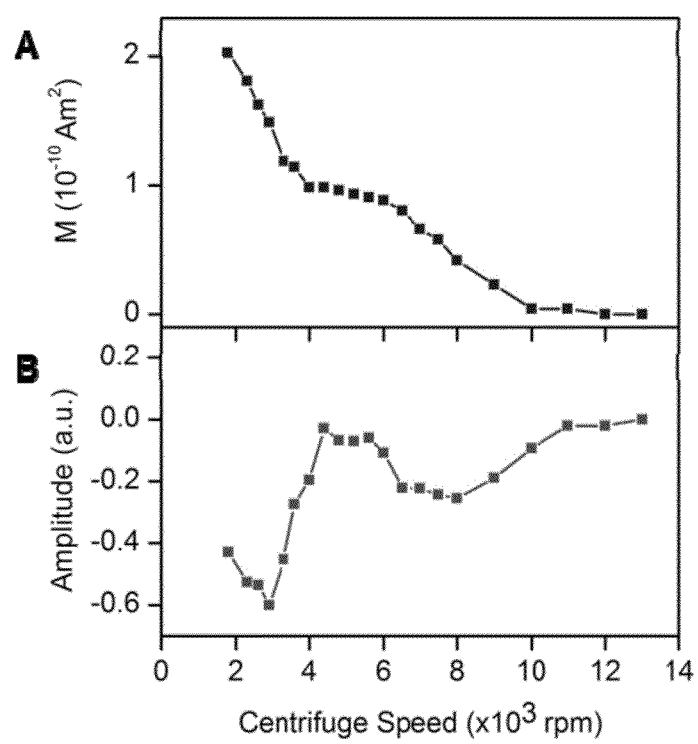
FIG. 9 depicts the force calibration of a FIRM spectrum using centrifugal force (9A), and the corresponding FIRM spectrum (9B)

FIG. 9 shows the results of the same experiment except that a centrifugal force is used. The force can be calculated according to $m\omega^2 r$, where m is the buoyance mass of the magnetic particle, ω is the speed, and r is the distance between the sample and the rotation center. All of these parameters can be obtained from standard methods. The resulting forces indicate that 18 pN is required to induce dissociation of the non-specifically bound conjugate and 129 pN force is required for dissociation of the specific IgG-α-IgG binding, which agrees with literature values.

Example 3

Rebinding Experiments

Figure 10:
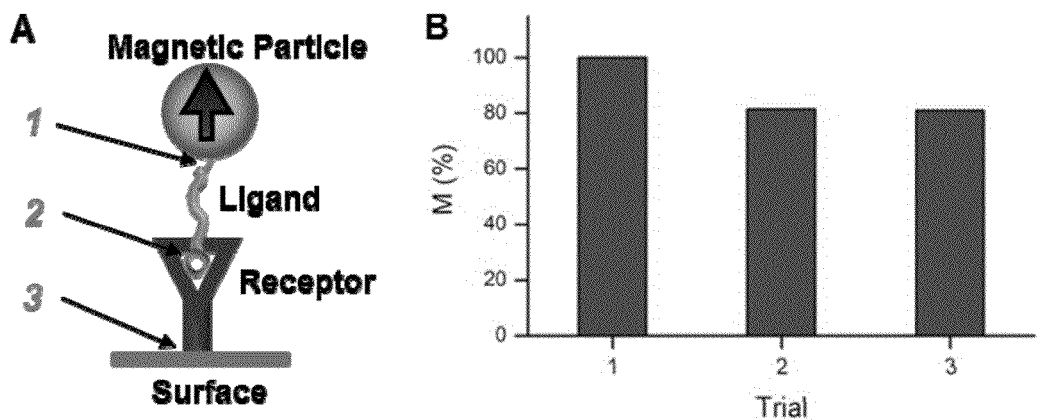
FIG. 10 depicts a schematic of three possible dissociation locations within a target-molecule-magnetic-particle-conjugate (10A).

Rebinding experiments were performed to confirm whether the dissociated bonds are the specific chemical bonds for diagnosis. It is believed that conventional technique cannot achieve this. As shown in FIG. 10A, there are three possible dissociation spots: 1 is between the ligand and the magnetic particle, 2 is the desired spot between the ligand and the receptor molecule, and 3 is between the receptor and the surface of biological sample or surface of the sample tray. Although position 2 is normally the weakest link for dissociation, no study has been performed to confirm this. Embodiments described herein allows for rebinding the biological sample with a second or more batches of ligand-coated magnetic particles and measuring the magnetization contrast accordingly. Only if the dissociation occurs at position 2 will magnetization contrast for specifically bound particles be obtained. The relative magnetization corresponding to the bound particles for the first trial and two rebinding attempts ($2^{nd}$ and $3^{rd}$ trials) are plotted in FIG. 10B). Magnetization of trial 2 is 82% of that of trial 1, and magnetization of trial 3 is 100% of that of trial 2. Therefore the dissociation is due to the specific bonding at position 2.

Example 4

Methods to Increase Applied Force to Tight Binding Pairs

Figure 11:
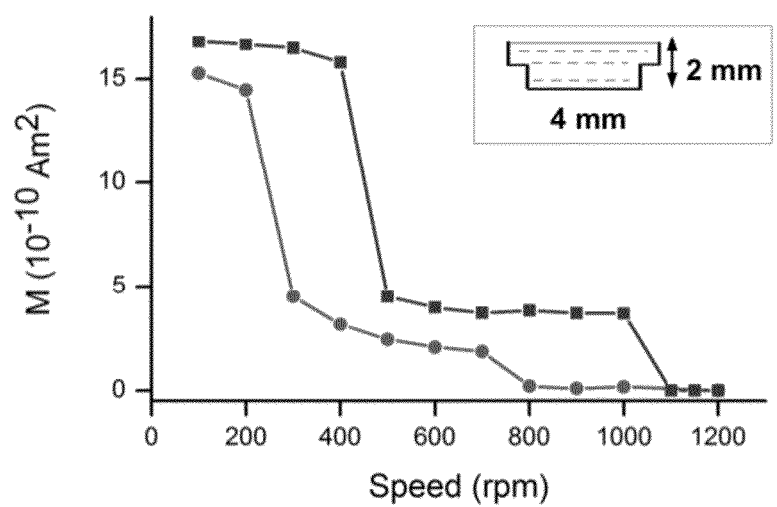
FIG. 11 illustrates the extension of the force range of a FIRMS method herein described by increasing the liquid level in the sample holder.

In some embodiments, the force range can be extended to investigate stronger molecular interactions. In one embodiment, this is achieved by increasing the liquid level in the sample holder. FIG. 11 compares results with 2 mm-level (circles) with the results with 1 mm-level (squares). From the shift of both dissociation speeds it can be concluded that the applied force is increased with a higher level of liquid in the sample holder.

Example 5

Methods to Investigate Specific Cell Targeting

Experiments were performed by some of the methods described in FIGS. 12A through 12I, herein to demonstrate the viability of embodiments of this method for cellular diagnosis with molecular specificity. A three component experiment was performed whereby the magnetization contrast and FIRM's spectra were measured for: 1) a blank, which contains streptavidin-coated magnetic particles in the sample holder; 2) cell binding, which contains streptavidin-coated magnetic particles, biotinylated-CD3 antibody, and human CD3+ T cells; and 3) streptavidin-coated magnetic particles and human CD3+ T cells, but absent of biotinylated-CD3 antibody. For specific cellular uptake of the magnetic particles to occur, the magnetic particles must bind to the biotinylated-CD3 antibody via the strong biotin-streptavidin interaction, then the CD3-coated magnetic particles bind to the cells via CD3 receptor. The cells naturally adhere to the bottom surface of the sample holder.

Figure 12:
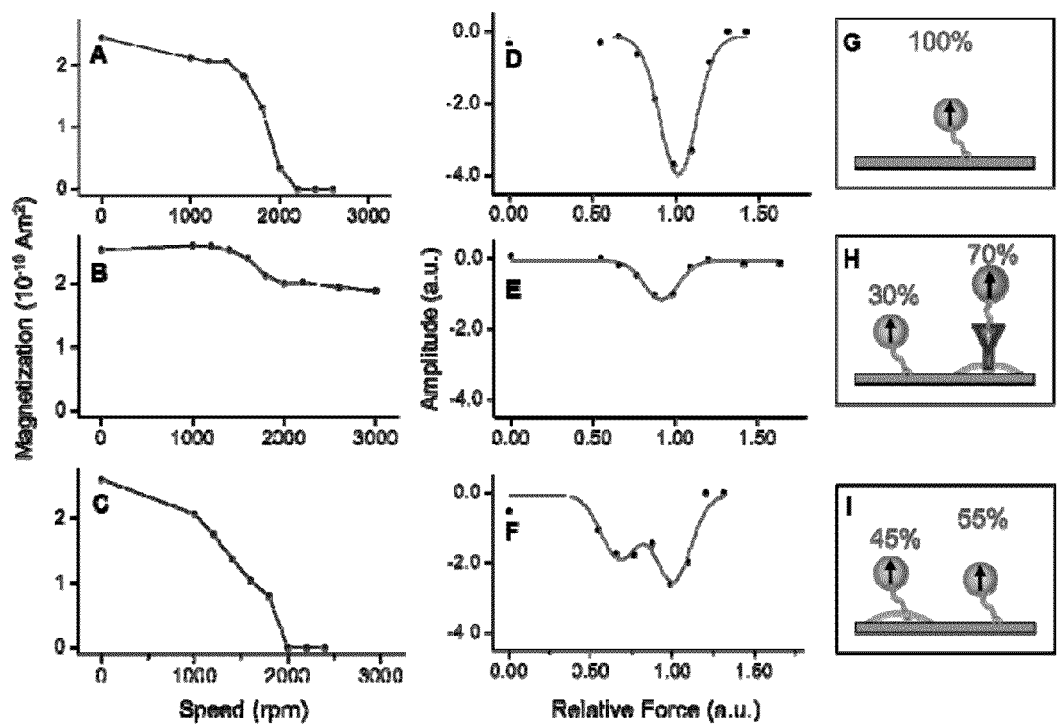
FIG. 12 illustrates the uptake of magnetic particle ligand conjugates by human CD3+ T cells. The magnetization contrast for blank; specific binding; and control respectively (12A, 12B, and 12C); 12D, 12E, and 12F are the FIRM spectra for 12A, 12B, and 12C, respectively. 12G, 12H and 12I depict the corresponding binding features with appropriate percentage amplitudes for 12A, 12B, and 12C, respectively.

FIGS. 12A, 12B and 12C, depict magnetization contrast measurements. FIGS. 12D, 12E and 12F are the corresponding FIRM spectra. FIGS. 12G, 12H and 12I depict the corresponding binding features with appropriate percentage amplitudes. In the blank experiment (FIGS. 12A, 12D and 12G), magnetic particles can only be physisorbed by the sample holder, as shown in FIG. 12A where the magnetization decreased to zero on application of a force centred at 1800 rpm. In the cell binding experiment, magnetization decreases to 70% of the initial value when the same force was applied, indicating 30% physisorption and 70% specific binding onto the cells. In the control experiment, where the magnetic particles can be physisorbed by both the sample holder surface and cell surface, two peaks are shown. One with 55% amplitude appears at the same position as the peak in the previous two experiments, indicating physisorption by the sample holder surface. The second, with 45% amplitude is due to physisorption by the cell surface. Therefore as predicted specific binding between the magnetic particles and cells are not possible due to the absence of biotynilated-CD3 antibody in experiment three.

Different binding features are clearly and quantitatively resolved based on their binding strength. Embodiments of the FIRMS method can selectively identify the quantity of magnetic particles that are specifically bound to the target molecules. The background signal from the physisorbed particles is effectively removed. For multiple target molecules, which may serve as indicators for different diseases, scanning the amplitude of the force will produce a spectrum of magnetization change vs. force that allows for the simultaneous detection and quantification of more than one disease in the same sample. The different molecules can be identified from their corresponding dips in the spectrum, if the binding forces between the magnetic particles and their corresponding target molecules are different. Embodiments described herein clearly display utility for identifying specific cells in biological samples and providing an accurate method of diagnosis of disease or the presence of toxic entities or prohibited substances that can be monitored due to the presence of biological markers.

While embodiments of the invention described here specifically focus on a novel method to detect molecules of interest based on their specific binding pairs and binding strength, one of ordinary skills in the art, with the benefit of this disclosure, will recognize the extension of the approach to other systems.

Depending on the context, all references herein to the "invention" or "method" may in some cases refer to certain specific embodiments only. In other cases, it may refer to subject matter recited in one or more, but not necessarily all, of the claims. While the foregoing is directed to embodiments, versions and examples of the present invention, which are included so as to enable a person of ordinary skill in the art to make and use the inventions when the information in this patent is combined with available information and technology, the inventions are not limited to only these disclosed particular embodiments, versions and examples. Other and further embodiments, versions and examples of the invention may be devised without departing from the basic scope thereof and the scope thereof is determined by the claims that follow.

What is claimed is:

1. A method of detecting target molecules species comprising;
    conjugating a first magnetic particle to a first ligand to form a first magnetic particle ligand conjugate;
    adding said conjugate to a sample containing target molecules to form a mixture comprising, non-specifically bound-conjugate and specifically bound conjugate-target molecule binding pairs;
    magnetizing the mixture with a magnetic field;
    measuring a first magnetization of said mixture;
    subjecting said mixture to a first mechanical force;
    measuring a second magnetization value of said mixture;
    subtracting said second magnetization value from said first magnetization value to calculate a first force-induced magnetization contrast;
    subjecting said mixture to a second mechanical force;
    measuring a third magnetization of said mixture; subtracting said third magnetization value from said second magnetization value to calculate a second force-induced magnetization contrast, and thereby performing a force scan, while measuring magnetization decrease as a function of the force and thereby detecting different target molecular species.

2. The method of claim 1, wherein said measuring comprises atomic magnetometers, superconducting quantum interference devices, giant magnetoresistive sensors, nuclear magnetic resonance, or combinations thereof.

3. The method of claim 1, wherein said mechanical force is produced by a shaker, centrifuge, sonicator, fluid stream, and combinations thereof.

4. The method of claim 1, wherein the force is scanned over a range of 5 pN to 2000 pN while measuring magnetization decrease as a function of the force.

5. The method of claim 4, whereby the force scan is produced by varying shaking speed, centrifugal speed, sound wave amplitude, or flow rate.

6. The method of claim 1, further comprising a second conjugate; wherein said second conjugate is different from said first conjugate, and said second conjugate forms a target molecule second conjugate binding pair, wherein said second conjugate binding pair produces a different FIRM peak than the first conjugate binding pair, thereby allowing the identification of different target molecules.

7. The method of claim 6, whereby the second conjugate differs from the first conjugate by chemical composition, shape, size, magnetic properties, ligand, magnetic coating properties or combinations thereof.

8. The method of claim 1, further comprising;
    plotting magnetization by force and calculating a derivative; and
    plotting the derivative of (a) by force to produce a force-induced remnant magnetization spectrum.

9. The method of claim 8, further comprising quantifying the number of peaks present in the spectrum and identifying the number of different target molecule species in the sample, based on said quantifying.

10. The method of claim 1, wherein said sample is selected from the group comprising natural molecules, synthetic molecules, biological tissue, biological cells or combinations thereof.

11. The method of claim 1 wherein said sample is immobilized on a surface, wherein said surface is derivatized or non-derivatized.

12. The method of claim 1, wherein said sample is an animal or human body and said adding is by injection or by ingestion.

13. The method of claim 1, wherein said sample is a chemical sample or biochemical sample for security checking.

14. The method of claim 1, wherein said sample is a chemical sample or biochemical sample in a toxicity screen.

15. The method of claim 1, wherein said magnetic field is provided by a permanent magnet or electrical magnet.

16. A method of detecting target molecules comprising:
    (a) conjugating a first magnetic particle to a first ligand to form a first magnetic particle ligand conjugate;
    (b) adding said conjugate to a sample containing target molecules to form a mixture comprising, 1) conjugate non specifically bound to the target molecule, and 2) conjugate chemically bound to the target molecule;
    (c) magnetizing the mixture with a magnetic field;
    measuring at least a first magnetization of said mixture;
    (d) subjecting said mixture to at least a first mechanical force;
    measuring a second magnetization value of said mixture;
    (e) subtracting said second magnetization value from said first magnetization value to calculate at least a first force-induced magnetization contrast; and (h) repeating steps (c)-(e) thereby performing a force scan, where the force is scanned over a range of about 5 pN to about 2000 pN, while measuring magnetization decrease as a function of the force and thereby detecting different target molecular species.

* * * * *